United States Patent [19]
Kraft

[11] Patent Number: 5,948,812
[45] Date of Patent: Sep. 7, 1999

[54] 1,7-DIOXACYCLOALKAN-8-ONE COMPOUNDS

[75] Inventor: Philip Kraft, Dübendorf, Switzerland

[73] Assignee: Givaudan Roure (International) SA, Vernier-Geneve, Switzerland

[21] Appl. No.: 09/076,950

[22] Filed: May 13, 1998

[30] Foreign Application Priority Data

Jun. 9, 1997 [EP] European Pat. Off. .............. 97109303

[51] Int. Cl.$^6$ .......................... A61K 31/365; A61K 7/46; C07D 321/00
[52] U.S. Cl. .............. 514/450; 512/12; 549/267
[58] Field of Search ............................ 549/267; 514/450; 512/12

[56] References Cited

U.S. PATENT DOCUMENTS

| | | | |
|---|---|---|---|
| 2,202,448 | 5/1940 | Firmenich | 260/344 |
| 2,234,551 | 3/1941 | Collaud | 260/344 |
| 4,251,448 | 2/1981 | Bauer et al. | 260/340.2 |

FOREIGN PATENT DOCUMENTS

| | | |
|---|---|---|
| 0 023612 | 2/1981 | European Pat. Off. . |
| 0 093852 | 11/1983 | European Pat. Off. . |
| 0 103893 | 3/1984 | European Pat. Off. . |

OTHER PUBLICATIONS

Brunn, H., et al. *Ernahrungs–Umschau*, 44(1997), Heft 1, 4–9.

Rimkus, G., et al. *Ernahrungs–Umschau*, 43(1996), Heft 12, 442–49.

Calkin, R.R., et al. *Perfumery–Practice and Principles*, (1994), 109–123.

*Primary Examiner*—Ba K. Trinh
*Attorney, Agent, or Firm*—Mark E. Waddell; Bryan Cave LLP

[57] ABSTRACT

Disclosed are odorant compounds having 14- to 17-membered 4-methyl substituted 1,7-dioxacycloalkan-8-ones and 14- to 16-membered 1,7-dioxacycloalkan-8-ones with 4,4-dimethyl substitution. Also disclosed are methods of odorizing a substance using at least one of the above mentioned compounds, as well as an economical process for their manufacture.

20 Claims, No Drawings

1,7-DIOXACYCLOALKAN-8-ONE COMPOUNDS

FIELD OF THE INVENTION

This invention is directed to 14- to 17-membered 4-methyl substituted 1,7-dioxacycloalkan-8-ones and 14- to 16-membered 4,4-dimethyl substituted 1,7-dioxacycloalkan-8-ones, the use of these compounds as odorants and a cost-effective process for their manufacture.

BACKGROUND OF THE INVENTION

Warm, sweet-powdery bottom notes with musk-like olfactory properties, which can extend from flowery-sweet (musk ambrette) via powdery-animalic (musk ketone) to even herby-woody tonalites (musk xylene), are almost indispensable in the composition of a perfume as well in the perfuming e.g. of cosmetics, washing and cleaning agents, conditioners or air fresheners. With regard to such olfactory characteristics and also because of their industrially simple and economical synthesis, aromatic musk substances have earned particular significance in perfumery and have been used universally and in high dosages. These compounds, especially musk xylene and musk ambrette, have, however, a certain toxicity, especially phototoxicity, as well as poor biological degradability. Depending on territorial regulations their use in new creations may be banned and have to be replaced by other compounds in old creations.

Other compounds with musk-like olfactory properties, especially toxicologically harmless macrocycles, are, however, significantly more expensive and have, inter alia, other side notes. Accordingly, when a nitromusk is replaced by a macrocycle the overall olfactory impression of a composition usually changes substantially. Moreover, the macrocycles which are commercially available today are by far not as facet-rich as the series of aforementioned highly substituted aromatics.

From the foregoing it will be evident that there exists a great need for novel non-toxic macrocyclic compounds with novel olfactory notes, especially such which are reminiscent of aromatic musk substances or with which similar facet-rich perfumistic effects can be produced. Moreover, such macrocyclic compounds should be simple and economical to manufacture in order that they can be used not only in luxury perfumes, but also in every day products, e.g. in cosmetics, washing and cleaning agents, conditioners or air fresheners.

SUMMARY OF THE INVENTION

The object of the present is to satisfy this need and to provide such compounds. Moreover, these compounds should be cost-effective to manufacture.

The object is achieved by the 4-methyl substituted 1,7-dioxacycloalkan-8-one class of compound, which satisfies the requisite demands in an ideal manner. They are represented by general formula I

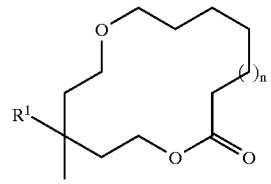

wherein $R^1$=H and n=1–4
or $R^1$=CH$_3$ and n=1–3.

The class of compounds in accordance with the invention accordingly embraces the 14- to 17-membered 1,7-dioxacycloalkan-8-ones with methyl substitution in the 4-position and the 14- to 16-membered 1,7-dioxacycloalkan-8-ones with dimethyl substitution in the 4-position. Compounds 1–16 are examples of the novel class of compounds, with the compounds having formulae 1, 3 and 4 being especially prominent organoleptically.

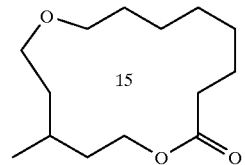

1

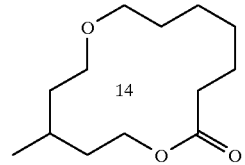

2

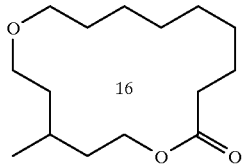

3

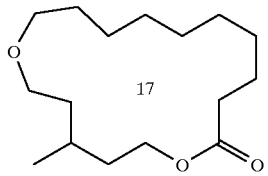

4

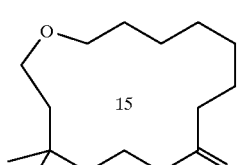

5

-continued

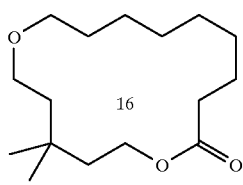

6

The compounds of general formula I have perfumistically interesting, powdery-warm, for the most part musk-like olfactory notes with fresh-floral to herb-like accents as well as good adhesion and good biological degradability. They are capable, alone or in combination with other macrocyclic odorants, of replacing questionably toxic compounds with the same or similar olfactory notes such as, for example, musk ambrette in the fields of use mentioned earlier. Further, having regard to their superior olfactory properties, they give, not only individually but also in combination, interesting new effects in new compositions. The olfactory notes thereby extend from the 14- to the 17-membered compounds from weakly musk-like, anise-like, herby, saffron, myrrh to strongly musk-like animalic. In particular, compounds 1, 3 and 4 are especially striking in this respect.

The compounds of general formula I harmonize with a large number of natural and synthetic products which are frequently used in odorant compositions. Especially in the chypre olfactory direction, for example in combination with a leathery accord, or in floral salicylate perfumes the compounds of general formula I give very interesting perfumistic effects. In particular, the compound 1 is ideally also suited for the composition of sweet fougère notes of the "Brut" (Fabergè, 1964) type and its more complex modern successors. The use is, however, limited neither to this type of perfume nor to special olfactory directions, odorants or classes of substance. Examples of classes of substance which harmonize especially well are:

- ethereal oils and extracts: e.g. castoreum, costusroot oil, oak moss absolute, geranium oil, jasmin absolute, patouli oil, rose oil, sandalwood oil or ylang-ylang oil;
- alcohols: e.g. citronellol, Ebanol®, eugenol, geraniol, Javanol®, linalool, phenylethyl alcohol, Sandalore®, terpineol or Timberol®;
- aldehydes and ketones e.g. alpha-amylcinnamaldehyde, Georgywood®, hydroxycitronellal, Iso-E-Super®, Isoraldein®, Hedion®, maltol, methylcedryl ketone, methylionone or vanillin;
- ethers and acetals: e.g. Ambrox®, geranyl methyl ether, rose oxide or Spirambrene®;
- esters and lactones: e.g. benzyl acetate, cedryl acetate, γ-decalactone, γ-undecalactone or vetiveryl acetate;
- macrocycles: e.g. ambrettolide, Musk TM II® or Exaltolid®;
- heterocycles: e.g. isobutylquinoline.

DETAILED DESCRIPTION OF THE PREFERRED EMBODIMENTS

The the 4-methyl substituted 1,7-dioxacycloalkan-8-one compounds of the present invention are represented by general formula I

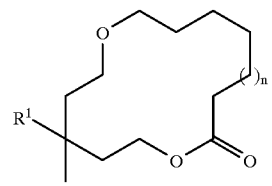

wherein $R^1$=H and n=1–4
or $R^1$=$CH_3$ and n=1–3.

The class of compounds in accordance with the invention accordingly embraces the 14- to 17-membered 1,7-dioxacycloalkan-8-ones with methyl substitution in the 4-position and the 14- to 16-membered 1,7-dioxacycloalkan-8-ones with dimethyl substitution in the 4-position. Compounds 1–16 are examples of the novel class of compounds, with the compounds having formulae 1, 3 and 4 being especially prominent organoleptically. At least one of the above mentioned compounds is used to produce an odorant composition.

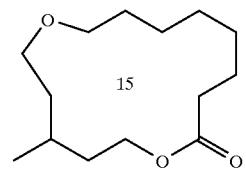

1

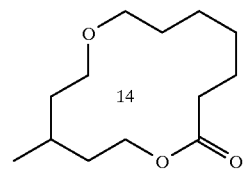

2

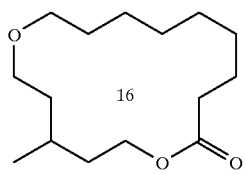

3

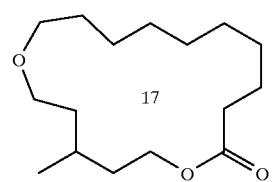

4

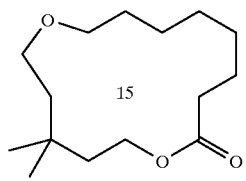

5

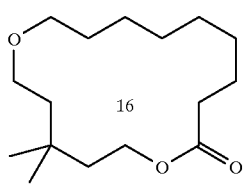

The present invention also provides a process for manufacturing a compound of formula I

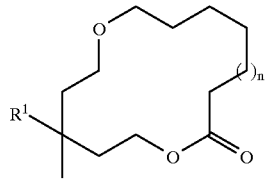

wherein $R^1$=H and n=1–4
or $R^1$=$CH_3$ and n=1–3 by polymerizing the hydromalonic ester having the formula 10

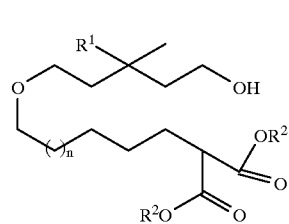

wherein n=1–4 and $R^2$ is an alkyl, preferably methyl or ethyl. The ester is polymerized by decarboxylation.

Accordingly, the present invention also provides a method of odorizing a substance by contacting a substance with at least one of the compounds of formula I. As used herein "substance" is considered to include air or any other substance of matter whether it is in the solid, liquid, or gaseous form. Also as used herein "contacting" includes evaporation, physical contacting, aspirating or any other form of contact.

The object of the cost-effective synthesis of the compounds of general formula I is achieved in accordance with the invention by a new access which starts from aliphatic dihalides and diols, which are readily accessible and economical starting materials. The synthesis sequence is based on a novel one-pot reaction comprising decarboxylation and cyclization which enables aliphatic hydroxymalonic esters to be cyclized directly to 14- to 17-membered macrolides.

The novel synthesis sequence to 14- to 17-membered oxamacrolides, via which especially the compounds of general formula I are accessible economically, begins, as presented schematically hereinafter, with the Williamson reaction of an aliphatic dihalide 7 with n=1–4 and X=Br or Cl and a diol 8, whereby $R^1$=H or Me for the synthesis of the compounds of general formula I, in the presence of a strong base, e.g. of sodium hydride. In addition to the dimeric condensation product 9, higher oligomers are also obtained, which, however, do not interfere with the further reaction, and accordingly the intermediate 9 need not be purified. Preferably, unused starting materials 7 and 8 are, after the reaction, separated by distillation for re-use.

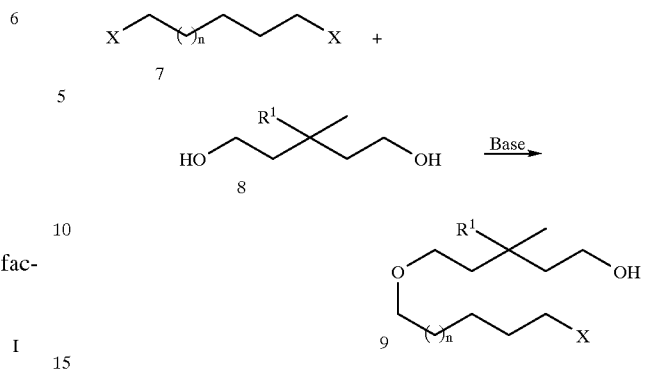

The next step of the sequence is a malonic ester condensation which is carried out in a known manner and which from the haloalcohol 9 yields the hydroxymalonic ester 10 in which $R^2$=alkyl, preferably Me or Et.

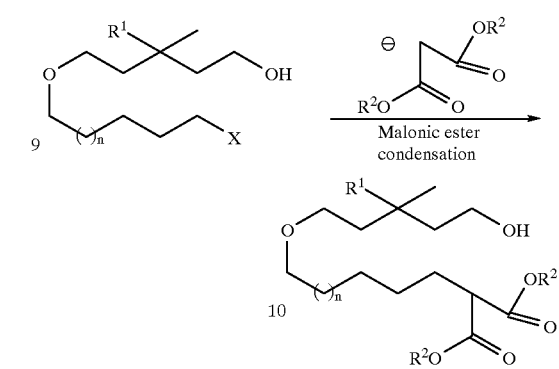

In accordance with the invention, the hydroxymalonic ester 10 is now without intermediary purification saponified in the novel one-pot reaction and polymerized with decarboxylation. The depolymerization and cyclization to the target compound, especially to a compound of general formula I, is effected by a known process, e.g. according to the process described in U.S. Pat. No. 2,234,551, which is herein incorporated by reference and is presented schematically hereinafter.

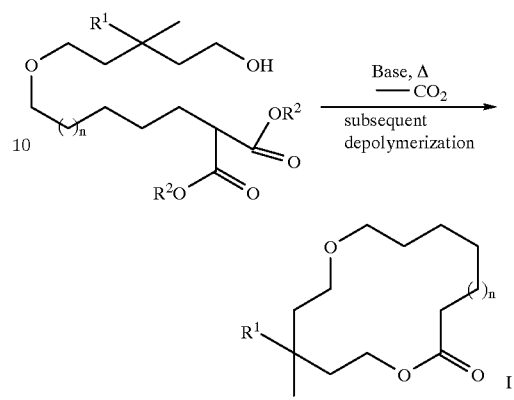

By the one-pot decarboxylation-polymerization and by the described synthesis sequence the use of expensive long-chain aliphatic halocarboxylic acids, which represents the major cost factor in the conventional synthesis of 14- to 17-membered oxamacrolides, is circumvented.

Although the described synthesis sequence is preferably directed to the manufacture of compound of general formula I, it can also be used in accordance with the invention for the economical manufacture of already known 14- to 17-membered oxamacrolides.

The compounds in accordance with the invention, preferably the compounds 1 to 6, especially the compounds 1, 3 and 4, particularly the compound 1, can be used individually or in combination as odorants. Particularly interesting olfactory effects are produced in an odorant composition when the respective compound is replaced by a content of about 0.1 to about 25 wt. %, preferably from 10 to 15 wt. %.

Further advantages, characteristics and particulars for illustrating the invention appear from the following description of preferred working examples:

EXAMPLES

The present invention is described further in the following examples which are presented solely for the non-limiting purpose of further illustrating the invention.

Example 1

Manufacture of 12-methyl-9-oxa-14-tetradecanolide (1)

118 g (1.0 mol) of 3-methyl-1,5-pentanediol and 317 g (1.3 mol) of 1,6-di-bromohexane in 2.5 l of dioxan were treated at room temperature with 28 g (1.1 mol) of 95 percent sodium hydride and subsequently heated under reflux for 24 h. After cooling the reaction mixture was treated with 400 ml of water, neutralized with saturated ammonium chloride solution and subsequently extracted three times with 1 l of tert-butyl methyl ether each time. The combined organic extracts were washed with saturated ammonium chloride solution, dried over magnesium sulphate and concentrated on a rotary evaporator. Starting material and byproducts were removed by distillation in a vacuum at 150° C. bath temperature and 0.09 mbar. As the distillation residue there were obtained 183 g of 66 percent 12-bromo-3-methyl-6-oxadodecan-1-ol (43%), which is sufficiently pure for the further reactions.

A sample, purified by bulb tube distillation at 200° C./0.03 mbar, shows the following spectroscopic data:

IR (film): $\nu$=1112 cm$^{-1}$ ($\nu_{as}$C—O—C), 1060 cm$^{-1}$ ($\nu_s$ C—O—C), 3389 cm$^{-1}$ ($\nu$O—H), 1459 cm$^{-1}$ ($\delta$C—H), 1377 cm$^{-1}$ ($\delta$CH$_3$).—$^1$H-NMR (CDCl$_3$): $\delta$=0.93 (d, J=6.8 Hz, 3H, 3-Me), 1.35–1.49 (m, 6H, 2-, 9-, 10-H$_2$) 1.55–1.65 (m, 4H, 4-, 8-H$_2$), 1.72 (oct, J=6.8 Hz, 1H, 3-H), 1.89 (quint, J=6.8 Hz, 2H, 11-H$_2$), 2.19 (br s, 1H, OH), 3.39–3.49 (m, 6H, 5-, 7-, 12-H$_2$), 3.65 (ddd, J=10.4,4.0 and 4.0 Hz, 1H, 1-H$_b$), 3.71 (ddd, J=10.4,3.7 and 3.7, 1H, 1-H$_a$). —$^{13}$C-NMR (CDCl$_3$): $\delta$=19.86 (q, 3-Me),25.30 (t, C-9), 26.76 (d, C-3), 27.89 (t, C-10), 29.42 (t, C-8),32.63 (t, C-12), 33.84 (t, C-11), 36.43 (t, C-4) 39.69 (t, C-2), 60.73 (t, C-1), 68.96 (t, C-5), 70.72 (t, C-7).—MS (EI): m/z (%)=83 (100) [C$_6$H$_{11}$$^\oplus$], 99 (61) [C$_6$H$_{11}$O$^\oplus$, 117 (7), [M$^\oplus$—C$_6$H$_{12}$Br], 163/165 (6) [M$^\oplus$—C$_6$H$_{13}$O$_2$], 263/265 (2) [M$^\oplus$—OH].

A solution of 30 g (520 mmol) of 95 percent sodium methylate in 220 ml of dry methanol was heated to reflux. Thereupon, 60 ml (520 mmol) of dimethyl malonate were allowed to drop in, the reaction mixture was heated under reflux for a further 15 min. and then 182 g of 66 percent 12-bromo-3-methyl-6-oxadodecan-1-ol from the preceding batch were added thereto. After heating under reflux for 14 hours the reaction mixture was added to 1.6 l of water/tert-butyl methyl ether (1:1) and made acid with concentrated phosphoric acid. The organic phase was separated and the aqueous phase was extracted twice with 500 ml of tert-butyl methyl ether each time. The combined organic phases were dried over magnesium sulphate, concentrated to dryness on a rotary evaporator, taken up in 400 ml of methanol and treated with 99 g (1.5 mol) of 85 percent potassium hydroxide. Methanol and byproducts were distilled off at 180° C./20–23mbar during 1 h. Thereupon, the reaction mixture was treated with 200 ml (2.4 mol) of 3-chloro-1,2-propanediol and heated to 140° C. for 1 h. After distilling off the excess 3-chloro-1,2-propanediol the reaction vessel was fitted with a condenser and separator and treated with 6.0 g (86 mmol) of potassium methylate in 450 ml of anhydrous glycerol. After stirring at 140° C./20–30 mbar for 15 minutes the mixture was heated to reflux at 155° C./4–6 mbar for 3 days under the separator, with 6.0 g (86 mmol) of potassium methylate being added every 24 hours. The separated glycerol was poured into 800 ml of water and extracted three times with 500 ml of tert-butyl methyl ether each time. After drying the combined organic extracts over magnesium sulphate, concentration on a rotary evaporator and distillation at 95–97° C./0.04 mbar there were obtained 59 g (52%) of 12-methyl-9-oxa-14-tetradecanolide (1) as a colorless liquid with the following characteristics.

Odor: Musk, flowery-woody, sweet-powdery, slightly anise-like, fresh, reminiscent of myrrh to musk ambrette, musk seed oil and tonkin musk.—IR (film):$\nu$=1735 cm$^{-1}$ ($\nu$C=O), 1116/1153 cm$^{-1}$ ($\nu_{as}$ O—C—C), 1247 cm$^{-1}$ ($\nu_{as}$ C—C(=O)—O), 1209 cm$^{-1}$ ($\nu_{as}$ C—O—C), 1352 cm$^{-1}$ ($\delta$CH$_3$), 1054 cm$^{-1}$ ($\nu_{as}$ C—O—C). —$^1$H-NMR (CDCl$_3$): $\delta$=0.94 (d, J=6.4 Hz, 3H, 12-Me), 1.27–1.76 (m, 14H, 3-H$_2$-7-H$_2$ and 11-13-H$_2$), 1.89 (oct, J=6.7 Hz, 1H, 12H), 2.34 (t, J=6.4 Hz, 2H, 2-H$_2$), 3.37–3.52 (m, 4H, 8-,10-H$_2$), 4.16 (ddd, J=11.2, 9.9 and 3.3 Hz, 1H, 14-H$_b$), 4.19 (ddd, J=11.2, 5.4 and 5.2 Hz, 1H, 14-H$_a$).—$^{13}$C-NMR (CDCl$_3$): $\delta$=19.22 (q, 12-Me), 24.46 (t, C-3), 24.95 (d, C-12), 25.92 (t, C-6), 27.02/28.12/28.44 (t, C-4,-5,-7), 33.89 (t, C-2), 35.45/36.62 (t, C-11,-13), 61.51 (t, C-14), 67.60/69.61 (t, C-8,-10), 173.91 (s, C-1).—MS (EI): m/z (%)=55 (100) [C$_4$H$_7$$^\oplus$], 83 (59) [C$_6$H$_{11}$$^\oplus$], 99 (24) [C$_6$H$_{11}$O$^\oplus$], 124 (31) [M$^\oplus$—H$_2$O—C$_6$H$_{12}$O], 141 (19) [M$^\oplus$—H$_2$O—C$_6$H$_{11}$], 213 (1) [M$^\oplus$—CHO], 242 (1)[M$^\oplus$]. —C$_{14}$H$_{26}$O$_3$ (242.36): calculated C 69.38, H 10.81; found C 69.24, H 10.68.

The following compounds have been manufactured in an analogous manner using dihalides 6 of different length. For them there are therefore set forth only the spectroscopic data, the olfactory characteristics and the elementary analyses:

Example 2

11-Methyl-8-oxa-13-tridecanolide (2)

Odor: Saffron, anise-like, woody-flowery, piny-terpene like, fresh, slightly musk-like. —IR (film):$\nu$=1734 cm$^{-1}$ ($\nu$C=O), 1123/1155 cm$^{-1}$ ($\nu_{as}$ O—C—C), 1254 cm$^{-1}$ ($\nu_{as}$ C—C(=O)—O), 1203 cm$^{-1}$($\nu_{as}$ C—O—C), 1357 cm$^{-1}$ ($\delta$CH$_3$), 1056 cm$^{-1}$ ($\nu_{as}$ C—O—C). —$^1$H-NMR (CDCl$_3$): $\delta$=0.96 (d, J=6.8 Hz, 3H, 11-Me), 1.15 (dddd, J=14.5, 10.0, 4.8 and 2.4 Hz, 1H, 12-H$_b$), 1.25–1.79 (m, 10H, 3-H$_2$-6-H$_2$, 10-H$_2$), 1.85 (dddd, J=14.5, 7.6, 7.3 and 3.9 Hz, 1H, 12-H$_a$), 1.99 (m$_c$, 1H, 11-H), 2.31 (ddd, J=14.8, 8.3 and 3.7 Hz, 1H, 2-H$_b$), 2.41 (ddd, J=14.8, 9.3 and 3.7 Hz, 1H, 2-H$_a$), 3.33–3.50 (m, 4H, 7-,9-H$_2$), 3.98 (ddd, J=11.2, 11.0 and 2.4 Hz, 1H, 13-H$_b$), 4.53 (ddd, J=11.2, 4.6 and 3.6 Hz, 1H, 13-H$_a$).—$^{13}$C-NMR (CDCl$_3$): $\delta$=19.47 (q, 11-Me), 23.72 (d, C-11), 25.32/25.51/26.81 (t, C-3-C-5), 28.62 (t, C-6), 33.79 (t, C-2), 34.53 (t, C-12), 36.51 (t, C-10), 60.96 (t, C-13), 66.91/68.85 (t, C-7,-9), 173.78 (s, C-1).—MS (EI): m/z (%)=55 (100) [$C_4H_7^{\oplus}$], 83 (79) [$C_6H_{11}^{\oplus}$], 101 (48) [$C_6H_{13}O^{\oplus}$], 111 (24) [$C_6H_{13}O^{\oplus}$]127 (30) [$M^{\oplus}$—$C_6H_{13}O$], 145 (4) [$M^{\oplus}$—$C_6H_{11}$], 169 (2) [$M^{\oplus}$—$C_2H_3O_2$], 199 (1) [$M^{\oplus}$—CHO], 228 (1) [$M^{\oplus}$].—$C_{13}H_{24}O_3$ (228.33): calculated C 68.38, H 10.60; found C 68.55, H 10.57.

Example 3

13-Methyl-10-oxa-15-pentadecanolide (3)

Odor: Musk, animalic, warm-powdery, flowery, slightly after saffron.—IR (film): n=1734 cm$^{-1}$ ($\nu$C=O), 1118/1151 cm$^{-1}$ ($\nu_{as}$O—C—C), 1250 cm$^{-1}$ ($\nu_{as}$ C—C(=O)—O), 1357 cm$^{-1}$($\delta$CH$_3$), 1061 cm$^{-1}$ ($\nu_{as}$ C—O—C).—$^1$H-NMR (CDCl$_3$): $\delta$=0.91 (d, J=6.4 Hz, 3H, 13-Me), 1.31–1.66 (m, 15H, 3-H$_2$-8-H$_2$, 12-H$_2$, 14-H$_b$), 1.83 (ddt, J=19.1, 9.6 and 5.0 Hz, 1H, 14-H$_a$), 1.93 (m$_c$, 1H, 13-H), 2.33 (dd, J=6.9 and 6.2 Hz, 2H, 2-H$_2$), 3.34–3.52 (m, 4H, 9-,11-H$_2$), 4.14 (ddd, J=11.0, 5.5 and 5.0 Hz, 1H, 15-H$_b$), 4.21 (ddd, J=11.0, 10.0 and 4.0 Hz, 1H, 15-H$_a$).—$^{13}$C-NMR (CDCl$_3$): $\delta$=18.22 (q, 13-Me), 24.67/25.26 (t, C-3,-7), 25.53 (d, C-13), 27.21/27.40/27.52 (t, C-4,-5,-6), 28.68 (t, C-8), 34.67 (t, C-2), 35.49 (t, C-14), 37.01 (t, C-12), 61.74 (t, C-15), 67.67/70.16 (t, C-9,-11), 173.93 (s, C-1).—MS (EI): m/z (%)=55 (100) [$C_4H_7^{\oplus}$], 83 (64) [$C_6H_{11}^{\oplus}$], 99 (30) [$C_6H_{11}O^{\oplus}$], 138 (25) [$M^{\oplus}$—$C_6H_{14}O_2$], 155 (23) [$M^{\oplus}$—$C_6H_{13}O$], 213 (2) [$M\oplus$—$C_2H_3O$], 227 (2) [$M^{\oplus}$—CHO], 256 (1) [$M^{\oplus}$].—$C_{15}H_{28}O_3$ (256,39): calculated C 70.27, H 11.01; found C 70.26, H 11.09.

Example 4

14-Methyl-11-oxa-16-hexadecanolide (4)

Odor: Animalic, musk, sweet, erogenous, warm-powdery.—IR (film): $\nu$=1735 cm$^{-1}$ ($\nu$C=O), 1117/1151 cm$^{-1}$ ($\nu_{as}$ O—C—C), 1254 cm$^{-1}$ ($\nu_{as}$ C—C(=O)—O), 1361 cm$^{-1}$ ($\delta$CH$_3$), 1060 cm$^{-1}$ ($\nu_{as}$ C—O—C).—$^1$H-NMR (CDCl$_3$): $\delta$=0.92 (d, J=6.8 Hz, 3H, 14-Me), 1.29–1.56 (m, 14H, 4-H$_2$-9-H$_2$, 13-H$_2$), 1.61–1.67 (m, 3-H$_2$, 15-H$_b$), 1.79 (ddt, 14.0, 8.4 and 5.2 Hz, 1H, 15-H$_a$), 1.87 (m$_c$, 1H, 14-H), 2.33 (dd, J=6.8 and 6.0 Hz, 2H, 2-H), 3.34–3.50 (m, 4H, 10-,12-H$_2$), 4.15 (ddd J=11.2, 6.0 and 5.2 Hz, 1H, 16-H$_b$), 4.18 (ddd, J=11.2, 8.4 and 4.4 Hz, 1H, 16H$_a$). —$^{13}$C-NMR (CDCl$_3$): $\delta$=18.54 (q, 14-Me), 24.80/26.15 (t, C-3,-8), 26.17 (d, C-14), 27.31/27.66/27.791/28.22 (t, C-4-C-7), 29.15 (t, C-9), 34.02 (t, C-2), 35.57 (t, C-15), 37.00 (t, C-13), 62.14 (t, C-16), 68.05/70.77 (t, C-10,-12), 174.14 (s, C-1). —MS (EI): m/z (%)=55 (100) [$C_4H_7^{\oplus}$], 83 (71) [$C_6H_{11}^{\oplus}$], 99 (33) [$C_6H_{11}O^{\oplus}$]113 (13) [$M^{\oplus}$—$C_{10}H_{21}O$]153 (15) [$M^{\oplus}$—$C_6H_{13}O_2$], 169 (16) [$M^{\oplus}$—$C_6H_{13}O$]171 (9) [$C_{10}H_{19}O_2^{\oplus}$], 227 (1) [$M^{\oplus}$—$C_2H_3O$], 241 (2) [$M^{\oplus}$—CHO], 270 (1) [$M\oplus$].—$C_{16}H_{30}O_3$ (270.41): calculated C 71.07, H 11.18; found C 71.37, H 11.13.

Example 5

12,12-Dimethyl-9-oxa-14-tetradecanolide (5)

Odor: Relatively weak, powdery musk-like, woody-herby.—IR (film): $\nu$=1734 cm$^{-1}$ ($\nu$C=O), 1117/1154 cm$^{-1}$ ($\nu_{as}$ O—C—C), 1252 cm$^{-1}$($\nu_{as}$ C—C(=O)—O), 1366 cm$^{31}$ 1($\delta$CH$_3$), 1046 cm$^{-1}$($\nu_{as}$ C—O—C).—$^1$H-NMR (CDCl$_3$): $\delta$=0.94 (s, 6H, 12-Me$_2$), 1.31–1.42 (m, 6H, 4-H$_2$-6-H$_2$), 1.50–1.57 (m, 4H, 3-,7-H$_2$), 1.69 (t, J=7.2 Hz, 2H, 11-H$_2$), 1.71 (dd, J=10.0 and 6.8 Hz, 2H, 13-H$_2$), 2.30 (t, J=6.6 Hz, 2-H$_2$), 3.39 (t, J=5.2 Hz, 8-H$_2$), 3.46 (t, J=6.2 Hz, 10-H$_2$), 4.16 (t, J=7.0 Hz, 2H, 14-H$_2$). —$^{13}$C-NMR (CDCl$_3$):

$\delta$=23.72, 24.91 (t, C-3,-6), 26.41/27.89 (t, C-4,-5), 28.59 (2q, 12-Me$_2$), 29.05 (t, C-7), 31.77 (s, C-12), 34.59 (t, C-2), 38.86/40.57 (t, C-11,-13), 61.93 (t, C-14), 67.66/69.88 (t, C-8,-10), 174.15 (s, C-1).—MS (El): m/z (%)=55 (100) [$C_4H_7^{\oplus}$], 69 (72) [$C_5H_{9\oplus}$], 81 (40) [$C_6H_9^{\oplus}$], 97 (59) [$C_6H_9O\oplus$]113 (27) [$C_7H_{13}O\oplus$]125 (27) [$C_8H_{13}O^{\oplus}$], 141 (15) [$M^{\oplus}$—$C_6H_9O$—$H_2O$], 183 (2) [$M^{\oplus}$—$C_4H_7$—$H_2O$] 227 (1)[$M^{\oplus}$—CHO], 256 (1) [$M\oplus$].—$C_{15}H_{28}O_3$ (256.39): calculated C 70.27, H 11.01; found C 70.15, H 10.87.

Example 6

13,13-Dimethyl-10-oxa-15-pentadecanolide (6)

Odorant: relatively weak, fruity-musk like, reminiscent of ambrettone.—IR (film): $\nu$=1734 cm$^{-1}$ ($\nu$C=O), 1118/1150 cm$^{-1}$($\nu_{as}$ O—C—C), 1242 cm$^{-1}$ ($\nu_{as}$ C—C(=O), 1365 cm$^{-1}$ (d CH$_3$), 1055 cm$^{-1}$ ($\nu$C—O—C).—$^1$H-NMR (CDCl$_3$): $\delta$=0.95 (s, 6H, 13-Me$_2$), 1.33–1.40 (m, 8H, 4-H$_2$-7-H$_2$), 1.49–1.55 (m, 4H, 8-,12-H$_2$), 1.62 (m$_c$, 2H, 3-H$_2$), 1.76 (t, J=8.0 Hz, 2H, 14-H$_2$), 2.32 (t, J=6.4 Hz, 2H, 2-H$_2$), 3.38 (t, J=5.2 Hz, 2H, 11-H$_2$), 3.47 (t, J=5.8 Hz, 2H, 9-H$_2$), 4.16 (t, J=8.0 Hz, 2H, 15-H$_2$). —$^{13}$C-NMR (CDCl$_3$): $\delta$=23.94/24.56 (t, C-3,-7), 25.84/26.36/26.52 (t, C-4,-5,-6), 28.04 (2q, 13-Me$_2$), 29.23 (t, C-8), 31.79 (s, C-13), 34.53 (t, C-2), 39.02 (t, C-14), 41.28 (t, C-12), 61.98 (t, C-15), 67.82/70.49 (t, C-9,-11), 173.83 (s, C-1). —MS (EI): m/z (%)=55 (100) [$C_4H_7^{\oplus}$]69 (92) [$C_5H_9^{\oplus}$], 113 (39) ]$C_8H_{17}^{\oplus}$], 139 (29) [$M^{\oplus}$—$C_7H_{15}O_2$], 155 (18) [$M^{\oplus}$—$C_7H_{15}O_2$], 197 (3) [$M^{\oplus}$—CO—$C_2H_4O$], 241 (2) [$M^{\oplus}$—CO], 270 (1) [$M\oplus$]—$C_{16}H_{30}O_3$ (270.41): calculated C 71.07, H 11.18; found C 70.89, H 11.11.

Example 7

A masculine perfume composition "Oriental Fougere" was produced. The components are listed below. For this, 15 wt. % of compound 1 was used in place of the musk ambrette which is usually used for this type of perfume composition. The composition contains no polycyclic musk odorants.

Compound 1 confers to the perfume a musk note, introduces sweetish-powdery effects reminiscent of nitromusk and therefore becomes more than a substitute for nitromusk. Its powderiness together with the tonkin musk aspect underlines the warm-powdery olfactory impression and contributes to the rounding-off of the top note and of the total composition.

| Composition | |
|---|---|
| Ingredients | Weight % |
| 1. Aldehyde C11 (10-undecen-1-al) | 0.05 |
| 2. Aldehyde C12 (lauric) | 0.05 |
| 3. α-Amylcinnamaldehyde | 1.0 |
| 4. Isoamyl salicylate | 60.0 |
| 5. Anisaldehyde | 30.0 |
| 6. Benzyl acetate extra | 20.0 |
| 7. Benzyl salicylate | 80.0 |
| 8. Bergamot oil Italian | 100.0 |
| 9. Citronellyl formate | 5.0 |
| 10. Civet absolute | 1.0 |
| 11. Coumarin pure crystalline | 7.0 |
| 12. Diethyl phthalate | 1.8 |
| 13. Dipropylene glycol | 129.9 |
| 14. Geraniol extra | 3.0 |
| 15. Geranium oil African | 70.0 |
| 16. Heliotropin crystalline | 30.0 |
| 17. Hydroxycitronellal | 90.0 |

-continued

| Ingredients | Weight % |
|---|---|
| 18. Lavender oil | 50.0 |
| 19. Lemon oil Italian | 50.0 |
| 20. Lemongrass oil rectified | 5.0 |
| 21. Linalool synthetic | 5.0 |
| 22. Linalyl acetate synthetic | 5.0 |
| 23. Methyl anthranilate extra | 3.0 |
| 24. Methyl β-naphthyl ketone | 3.0 |
| 25. γ-Undecalactone | 0.1 |
| 26. Petitgrain oil Paraguay pure | 20.0 |
| 27. Phenylacetaldehyde 85%/PEA | 0.1 |
| 28. Phenylethyl alcohol white | 15.0 |
| 29. Sandalwood oil East Indian | 20.0 |
| 30. Tarragon oil | 25.0 |
| 31. Terpineol pure | 3.0 |
| 32. Vanillin | 7.0 |
| 33. Vetiver oil (Bourbon) | 10.0 |
| 34. Compound 1 | 150.0 |
| | 1000.0 |

Example 8

A masculine perfume composition "Fresh Musk" was produced. 10 wt. % of compound 1 were used in analogy to Example 7. The components are listed below.

Compound 1 intensifies the musk character and adds a note reminiscent of nitromusk. The additional myrrh-jasmone aspect moderates the herb-spicy top note and thereby gives it completely new facets. Thus, compound 1 harmonizes very well and synergistically with other macrocyclic musk odorants, e.g. especially with cyclopentadecanolide, and can combine well with flowery notes such as e.g. jasmin.

Composition

| Ingredients | Weight % |
|---|---|
| 1. Agrudor BAV 645/3 | 15.0 |
| 2. Ambrettone (Musk TM II) | 4.0 |
| 3. Benzyl acetate extra | 5.0 |
| 4. Benzyl salicylate | 120.0 |
| 5. Cepionate (Hedion) | 5.0 |
| 6. Dipropylene glycol | 480.0 |
| 7. Ethylene brassylate | 200.0 |
| 8. Hexyl cinnamaldehyde | 25.0 |
| 9. Lavender oil (Grosso) | 5.0 |
| 10. Lemon oil Italian | 5.0 |
| 11. Linalyl acetate synthetic | 25.0 |
| 12. Cyclopentadecanolide | 10.0 |
| 13. Tonka bean resinoid N.1 30%/DPG | 1.0 |
| 14. Compound 1 | 100.0 |
| | 1000.0 |

Example 9

A perfume oil with a modern lavender note, rounded off by fine flowery musk-like woody tones, for use in soaps was produced; it contained 10 wt. % of compound 1 in place of nitromusk otherwise usually used for this olfactory type.

The components of the composition are listed hereinafter.

The composition confers to the soap a very warm-powdery, pleasant effect, which, when the soap is used, underlines the cleansing and caring character.

Composition

| Ingredients | Weight % |
|---|---|
| 1. Acetaldehyde phenethylpropyl acetal 10% DPG | 25.0 |
| 2. Allyl phenoxyacetate | 5.0 |
| 3. Aldehyde C10 (n-decanal) | 6.0 |
| 4. Aldehyde C11 (10-undecenal) 10% DPG | 10.0 |
| 5. Aldehyde C12 (lauric) | 10.0 |
| 6. Aldehyde C12 NMA 10% DPG | 32.0 |
| 7. Allyl amyl glycolate | 8.0 |
| 8. Allyl capronate | 3.0 |
| 9. Bergamyl acetate | 25.0 |
| 10. Cinnamaldehyde | 2.0 |
| 11. Citronellal | 5.0 |
| 12. Citronellol 750 | 30.0 |
| 13. Coumarin pure crystalline | 5.0 |
| 14. Cyclamen aldehyde extra | 5.0 |
| 15. Dihydromyrcenol | 110.0 |
| 16. Ethylvanillin 10% DPG | 5.0 |
| 17. Eucalyptol | 5.0 |
| 18. Eugenol pure | 5.0 |
| 19. 3,6-Dimethyl-β-resocin acid methyl ester | 2.0 |
| 20. Florhydral | 5.0 |
| 21. Fructone | 5.0 |
| 22. Galbanum oil 10% DPG | 15.0 |
| 23. Geranitril T | 15.0 |
| 24. Geranium oil African | 15.0 |
| 25. α-Hexylcinnamaldehyde | 70.0 |
| 26. 2,4,6-Trimethyl-3-cyclohexene-1-carboxaldehyde | 9.0 |
| 27. Lavender oil (Grosso) | 15.0 |
| 28. Lilial | 120.0 |
| 29. Limettene oxide | 10.0 |
| 30. Linalool synthetic | 20.0 |
| 31. Menthanyl acetate | 25.0 |
| 32. Menthyl acetate | 15.0 |
| 33. para-tert-Butylcyclohexyl acetate | 60.0 |
| 34. Patchouli oil | 18.0 |
| 35. Phenylethyl acetate | 10.0 |
| 36. Phenylethyl alcohol white | 30.0 |
| 37. Rose oxide CO 10% DPG | 5.0 |
| 38. Rosemary oil | 5.0 |
| 39. Peppermint oil FCC NF extra KPF 10% DPG | 10.0 |
| 40. Terpineol pure | 50.0 |
| 41. Terpinyl acetate | 15.0 |
| 42. Tricylal 10% DPG | 10.0 |
| 43. Tridecenonitrile 10% DPG | 10.0 |
| 44. Verdol 10% DPG | 15.0 |
| 45. ortho-tert-Butylcyclohexyl acetate | 10.0 |
| 46. 1-Methyl-4-(4-methyl-3-pentenyl)-3-cyclohexene-1-carboxaldehyde | 15.0 |
| 47. Compound 1 | 100.0 |
| | 1000.0 |

Analogous compositions to the compositions described in Examples 7 to 9 were also produced with compounds 3 and 4.

From all of these exemplified compositions it will be evident that the class of compound in accordance with the invention, especially at least of one of compounds 1, 3 and 4, preferably compound 1, is outstandingly suitable for use as odorants.

While the invention has been illustrated and described with respect to illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

We claim:
1. Compounds of formula I

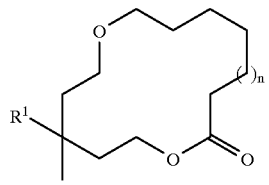

wherein $R^1$=H and n=1–4
or $R^1$=$CH_3$ and n=1–3.

2. A compound according to claim 1 identified as 12-Methyl-9-oxa-14-tetradecanolide.

3. A compound according to claim 1 identified as 11-Methyl-8-oxa-13-tridecanolide.

4. A compound according to claim 1 identified as 13-Methyl-10-oxa-15-pentadecanolide.

5. A compound according to claim 1 identified as 14-Methyl-11-oxa-16-hexadecanolide.

6. A compound according to claim 1 identified as 12,12-Dimethyl-9-oxa-14-tetradecanolide.

7. A compound according to claim 1 identified as 13,13-Dimethyl-10-oxa-15-pentadecanolide.

8. A method of odorizing a substance comprising contacting a substance with at least one of the compounds of claim 1.

9. A method of odorizing a substance comprising contacting a substance with at least one of the compounds selected from the group consisting of 12-Methyl-9-oxa-14-tetradecanolide, 11-Methyl-8-oxa-13-tridecanolide, 13-Methyl-10-oxa-15-pentadecanolide, 14-Methyl-11-oxa-16-hexadecanolide, 12,12-Dimethyl-9-oxa-14-tetradecanolide, and 13,13-Dimethyl-10-oxa-15-pentadecanolide.

10. A method of odorizing a substance comprising at least one of the compounds selected from the group consisting of 12-Methyl-9-oxa-14-tetradecanolide, 13-Methyl-10-oxa-15-pentadecanolide, and 14-Methyl-11-oxa-16-hexadecanolide.

11. A method of odorizing according to claim 8, wherein the odorizing compound is 12-methyl-9-oxa-14-tetradecanolide.

12. An odorant composition comprising at least one of the compounds of claim 1.

13. An odorant composition comprising at least one of the compounds selected from the group consisting of 12-Methyl-9-oxa-14-tetradecanolide, 11-Methyl-8-oxa-13-tridecanolide, 13-Methyl-10-oxa-15-pentadecanolide, 14-Methyl-11-oxa-16-hexadecanolide, 12,12-Dimethyl-9-oxa-14-tetradecanolide, and 13,13-Dimethyl-10-oxa-15-pentadecanolide.

14. An odorant composition comprising at least one of the compounds selected from the group consisting of 12-Methyl-9-oxa-14-tetradecanolide, 13-Methyl-10-oxa-15-pentadecanolide, and 14-Methyl-11-oxa-16-hexadecanolide.

15. An odorant composition according to claim 12 containing the compound 12-methyl-9-oxa-14-tetradecanolide.

16. An odorant composition according to claim 12, wherein the compounds are present in an amount of from about 0.1 to about 25%.

17. An odorant composition according to claim 12, wherein the compounds are present in an amount of from about 10 to about 15%.

18. A process for the manufacture of a compound of formula I

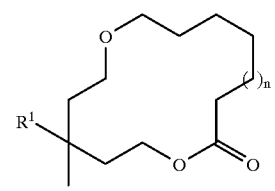

wherein $R^1$=H and n=1–4
or $R^1$=$CH_3$ and n=1–3,
comprising polymerizing the hydroxymalonic ester having the formula 10

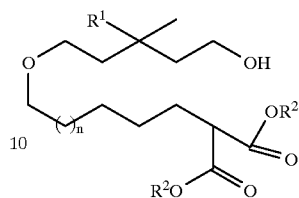

wherein n=1–4 and $R^2$=alkyl.

19. A process according to claim 18, wherein $R^2$ is methyl or ethyl.

20. A process according to claim 18, wherein the ester is polymerized by decarboxylation.

* * * * *